(12) United States Patent  (10) Patent No.: US 8,256,274 B2
Kukita et al.  (45) Date of Patent: Sep. 4, 2012

(54) SENSING DEVICE (75) Inventors: Hiroyuki Kukita, Saitama (JP);
Shunichi Wakamatsu, Sayama (JP)

(73) Assignee: Nihon Dempa Kogyo Co., Ltd., Tokyo (JP)

( * ) Notice: Subject to any disclaimer, the term of this patent is extended or adjusted under 35 U.S.C. 154(b) by 291 days.

(21) Appl. No.: 12/449,857

(22) PCT Filed: Mar. 6, 2008

(86) PCT No.: PCT/JP2008/054551
§ 371 (c)(1),
(2), (4) Date: Aug. 31, 2009

(87) PCT Pub. No.: WO2008/111624
PCT Pub. Date: Sep. 18, 2008

(65) Prior Publication Data
US 2010/0095751 A1 Apr. 22, 2010

(30) Foreign Application Priority Data
Mar. 6, 2007 (JP) ................................. 2007-054973

(51) Int. Cl.
*G01N 13/00* (2006.01)
(52) U.S. Cl. ..................... 73/64.53; 73/61.49; 73/61.75; 73/61.79; 73/579
(58) Field of Classification Search ................. 73/24.01, 73/24.03, 24.06, 61.45, 61.49, 61.75, 61.79, 73/64.53, 579
See application file for complete search history.

(56) References Cited

U.S. PATENT DOCUMENTS

| | | | | |
|---|---|---|---|---|
| 3,260,104 A | * | 7/1966 | King, Jr. | 73/24.06 |
| 3,266,291 A | * | 8/1966 | King, Jr. | 73/24.06 |
| 3,327,519 A | * | 6/1967 | Crawford | 73/24.06 |
| 3,329,004 A | * | 7/1967 | King, Jr. | 73/24.06 |
| 3,385,100 A | * | 5/1968 | Michael | 73/23.4 |
| 3,879,992 A | * | 4/1975 | Bartera | 73/24.01 |
| 4,227,182 A | * | 10/1980 | Ogasawara et al. | 340/870.37 |
| 5,705,399 A | * | 1/1998 | Larue | 436/501 |
| 5,852,229 A | * | 12/1998 | Josse et al. | 73/24.06 |
| 2008/0129148 A1 | * | 6/2008 | Wakamatsu et al. | 310/319 |
| 2008/0156097 A1 | * | 7/2008 | Onishi et al. | 73/579 |

FOREIGN PATENT DOCUMENTS

| | | |
|---|---|---|
| JP | 5-209861 | 8/1993 |
| JP | 6-167435 | 6/1994 |
| JP | 2004-340766 | 12/2004 |
| JP | 2005-331443 | 12/2005 |
| JP | 2006-258787 | 9/2006 |

* cited by examiner

*Primary Examiner* — Daniel Larkin
(74) *Attorney, Agent, or Firm* — Jordan and Hamburg LLP (57) ABSTRACT

Time-series data of piezoelectric resonator frequencies for each concentration of a substance to be absorbed is collectively displayed. An absorption start point of a substance to be absorbed is set in pieces of the time-series data. An editor combines and displays at least frequency variation regions in the data. The absorption start point setting is realized when an operator positions a pointer and clicks on the time-series data, or when an absorption start signal is output at the time when a solution is supplied.

4 Claims, 12 Drawing Sheets

MEASUREMENT PAGE 1

SENSING DEVICE

TECHNICAL FIELD

The present invention relates to a sensing device using a piezoelectric resonator whose natural frequency is varied by an absorption of a substance to be absorbed, and particularly relates to a technology to collectively display frequency variations of the piezoelectric resonators obtained for each concentration of the substance to be absorbed.

BACKGROUND ART

Figure 17:
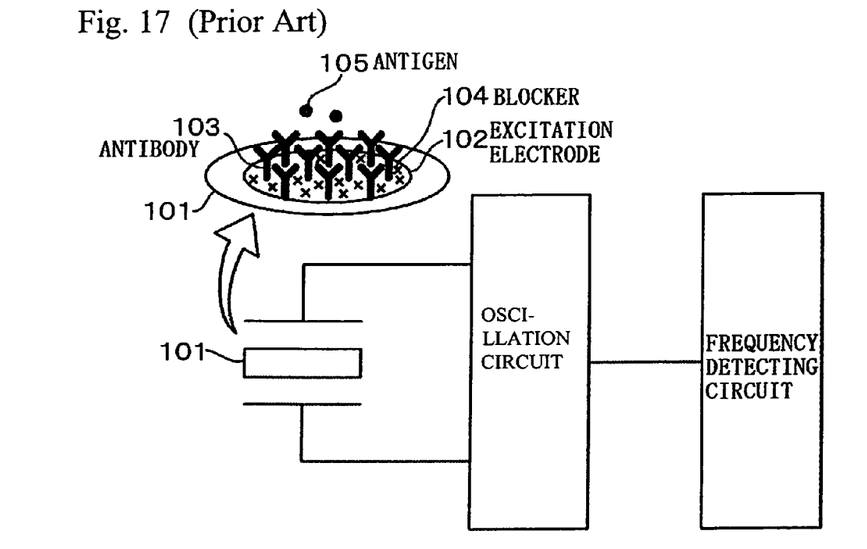
FIG. 17 is an explanatory diagram showing a conventional quartz sensor.

In a quartz resonator used for a bio-related sensing device, antibodies 103 capturing antigens by an antigen-antibody reaction are formed as an absorption layer on an excitation electrode 102 in a film shape formed on a surface of a quartz piece 101, and blocking substances (blockers 104) such as, for instance, proteins are absorbed into spaces among the antibodies 103, as shown in FIG. 17. Further, when antigens 105 are absorbed into the absorption layer, the natural frequency of the quartz resonator varies in accordance with an absorption amount of the antigens 105.

A manufacturing method of such a quartz resonator will be briefly described. A buffer solution is supplied into a quartz sensor having a quartz resonator on a bottom portion thereof, and subsequently, a solution containing a predetermined amount of antibodies 103 is supplied into the quartz sensor, to thereby make the antibodies 103 absorbed into a surface of the excitation electrode 102. Next, under this state, a solution containing a predetermined amount of blockers 104 is injected into the quartz sensor to make the blockers 104 absorbed into the surface of the excitation electrode 102. The reason why the blockers 104 are previously absorbed into the excitation electrode 102 is to prevent the antigens from being absorbed into the surface of the excitation electrode 102 to secure an accuracy of correspondence between a capturing amount of the antigens and frequencies. A frequency variation of the quartz resonator at the time of manufacturing the quartz sensor and a frequency variation at the time of measurement using the manufactured quartz sensor are sequentially shown in FIG. 18.

In the manufacturing stage of the aforementioned quartz sensor, it is necessary to know how much the frequency of the quartz resonator is lowered depending on which level the concentration of the antibodies 103 is set. Accordingly, it is convenient if pieces of time-series data of frequencies of the quartz resonators obtained for each concentration of the antibodies 103 in solutions are displayed on one screen. Further, also in the measurement stage using the manufactured quartz sensor, it is necessary to know how much the frequency of the quartz resonator is lowered depending on which level the concentration of the antigens 105 is set. Similarly, in this case, it is convenient if pieces of time-series data of frequencies of the quartz resonators obtained for each concentration of the antigens 105 in solutions are displayed on one screen. However, there is a problem that an operation to extract only the frequency variation amount (Δf) from a start of the absorption until an end of the absorption from the time-series data on each screen obtained for each concentration and edit the pieces of data on one screen requires much labor and time, and this is quite troublesome for an operator.

Meanwhile, Patent Document 1 describes that in a sample analyzer that performs a sample concentration measurement using a biosensor, the measured results regarding the sample concentration are input into a personal computer, and various statistical processes are performed on the input data using the computer, but, no reference is made regarding a concrete method for the statistical processes.
Patent Document 1
Japanese Patent Application Laid-open No. Hei 5-209861 (Paragraph 0008, FIG. 1)

DISCLOSURE OF THE INVENTION

The present invention has been made in view of such circumstances, and an object thereof is to provide a sensing device capable of easily and collectively displaying, based on pieces of time-series data of frequencies of piezoelectric resonators obtained for each concentration of a substance to be absorbed in solutions, pieces of variation data of the frequencies for each concentration caused by an absorption of the substance to be absorbed, in a state of aligning absorption start points.

A sensing device of the present invention is characterized in that it includes: a sensing sensor provided with a sensing piezoelectric resonator whose natural frequency is varied by an absorption of a substance to be absorbed; an oscillation circuit for oscillating the piezoelectric resonator; a display section for displaying pieces of time-series data of frequencies of the piezoelectric resonators obtained for each concentration of the substance to be absorbed in solutions supplied to the piezoelectric resonators; a unit for setting an absorption start point of the substance to be absorbed in the pieces of time-series data; and an editor for performing processing to combine and display at least frequency variation regions in the pieces of time-series data in a state of aligning the absorption start points of the substance to be absorbed.

In the aforementioned sensing device, it is preferable to structure such that the pieces of time-series data of the frequencies of the piezoelectric resonators obtained for each concentration of the substance to be absorbed in the solutions are respectively displayed on different pages. Further, the setting conducted by the unit for setting the absorption start point of the substance to be absorbed may be realized when, for instance, an operator positions a pointer and clicks on the time-series data displayed on the display section, or when the solution is supplied to the sensing sensor. Further, the unit for setting the absorption start point is, for example, a switch operated by an operator.

If the setting of the absorption start point is automatically performed when the solution is supplied to the sensing sensor, or if the setting is performed when the switch is operated by the operator, it is not necessary to display the pieces of time-series data of the frequencies of the piezoelectric resonators obtained for each concentration of the substance to be absorbed. The invention in this case is structured as follows.

A sensing device of another invention is characterized in that it includes: a sensing sensor provided with a sensing piezoelectric resonator whose natural frequency is varied by an absorption of a substance to be absorbed; an oscillation circuit for oscillating the piezoelectric resonator; a unit for obtaining pieces of time-series data of frequencies of the piezoelectric resonators obtained for each concentration of the substance to be absorbed in solutions supplied to the piezoelectric resonators; a unit for setting an absorption start point of the substance to be absorbed in the pieces of time-series data; and an editor for performing processing to combine and display at least frequency variation regions in the pieces of time-series data in a state of aligning the absorption start points of the substance to be absorbed.

According to the present invention, it is structured such that the absorption start point is set in the pieces of time-series data of the frequencies of the piezoelectric resonators obtained for each concentration of the substance to be absorbed such as, for instance, antibodies previously absorbed into the piezoelectric resonators and antigens captured by the antibodies in the manufacturing stage or the measurement stage, and the combined data in which the pieces of time-series data are combined based on the absorption start points is displayed. Accordingly, for example, the correspondence between the concentration of the substance to be absorbed which is absorbed into the piezoelectric resonator and the variation of frequencies, and the maximum absorption amount of the substance to be absorbed can be easily determined, which is very convenient in the manufacturing stage of the sensing sensor or the measurement stage using the sensing sensor.

BEST MODE FOR CARRYING OUT THE INVENTION

Figure 1:
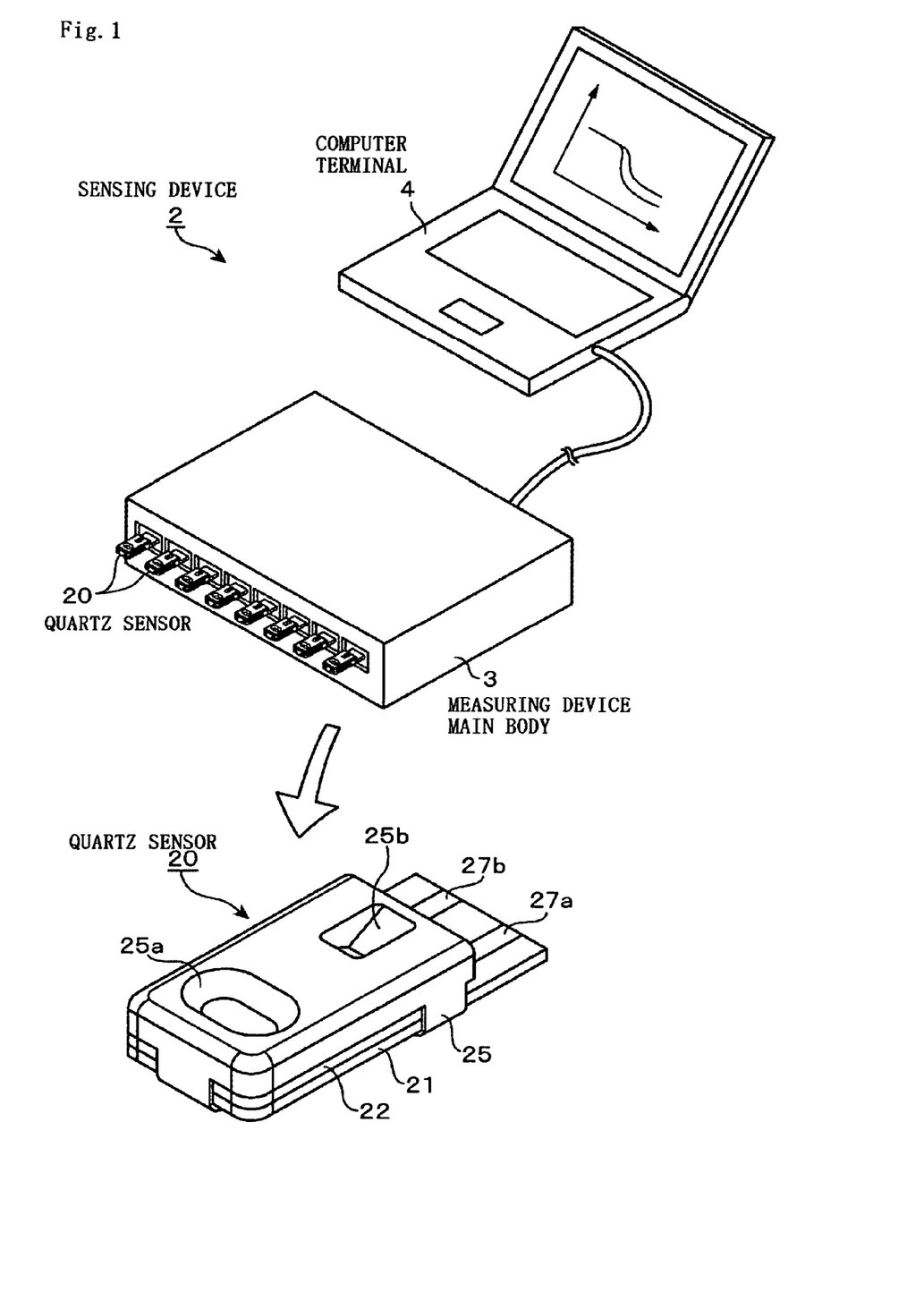
FIG. 1 is a whole structural diagram of a sensing device according to an embodiment of the present invention.

Embodiments of the present invention will be described. 2 in FIG. 1 is a sensing device, and the sensing device 2 is formed of a plurality of, for example, eight quartz sensors 20, a measuring device main body 3 to which the quartz sensors 20 are attachably/detachably mounted and including oscillation circuits 31, and a computer terminal 4 connected to the measuring device main body 3.

Figure 2:
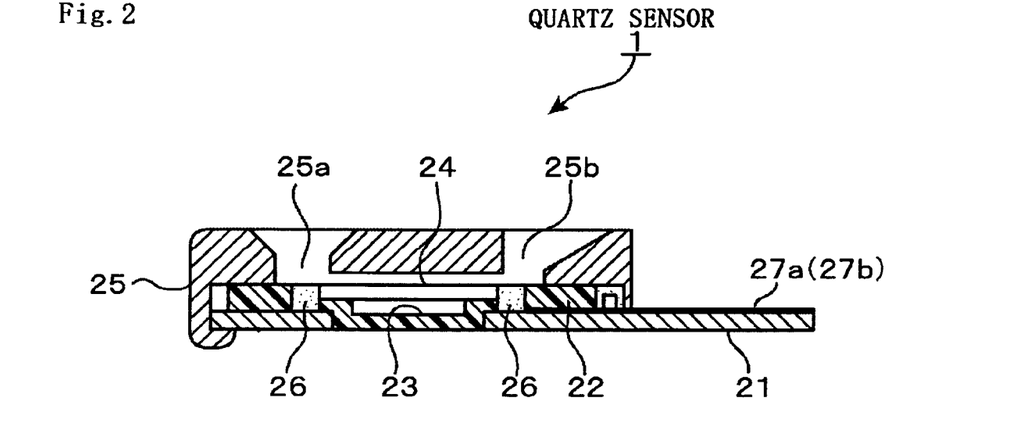
FIG. 2 is a vertical side view of a quartz sensor that composes the sensing device.

As shown in FIG. 1 and FIG. 2, the quartz sensor 20 includes a printed circuit board 21 which is a wiring board, a rubber sheet 22 stacked on the printed circuit board 21, a quartz resonator 24 as a piezoelectric resonator provided to close a recessed portion 23 provided in the rubber sheet 22, and an upper cover case 25 mounted from above the rubber sheet 22. In the upper cover case 25, an injection port 25a for a sample solution and a check port 25b for the sample solution are formed, and the sample solution is injected from the injection port 25a, so that a space on an upper surface side of the quartz resonator 24 is filled with the sample solution. The recessed portion 23 forms an airtight space on a lower surface side of the quartz resonator 24, whereby a Langevin-type quartz sensor is formed.

Figure 3:
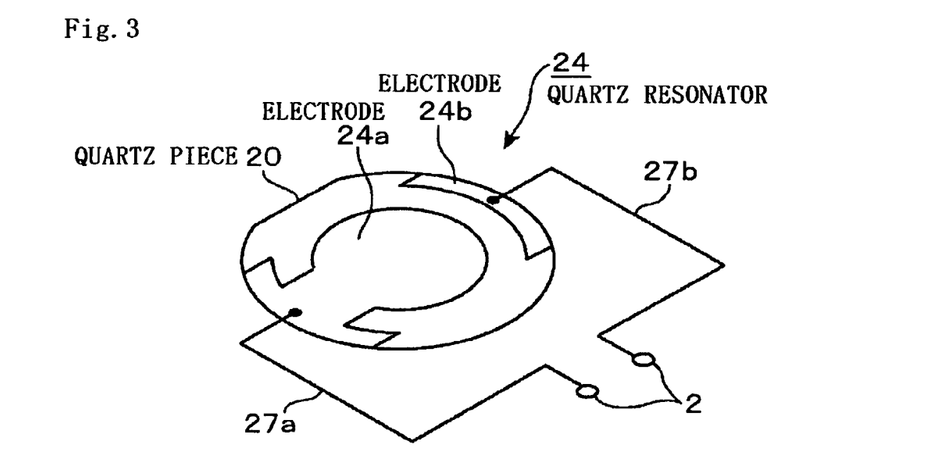
FIG. 3 is an explanatory diagram of a quartz resonator that composes the quartz sensor.

As shown in FIG. 3, in the quartz resonator 24, electrodes 24a and 24b are provided respectively on both surfaces of a quartz piece 20 in, for example, a circular shape (the rear surface-side electrode 24b is formed continuously from a front surface-side peripheral edge portion). Further, as explained in the description of the related art using FIG. 17, on the electrode 24a of the front surface side, antibodies capturing antigens by an antigen-antibody reaction are formed as an absorption layer, and blocking substances (blockers) such as, for instance, proteins are absorbed into spaces among the antibodies. The electrodes 24a and 24b are electrically connected via conductive adhesives 26, as shown in FIG. 2, to printed wirings 27a and 27b, respectively, which are a pair of conductive paths provided in the board 21.

Figure 4:
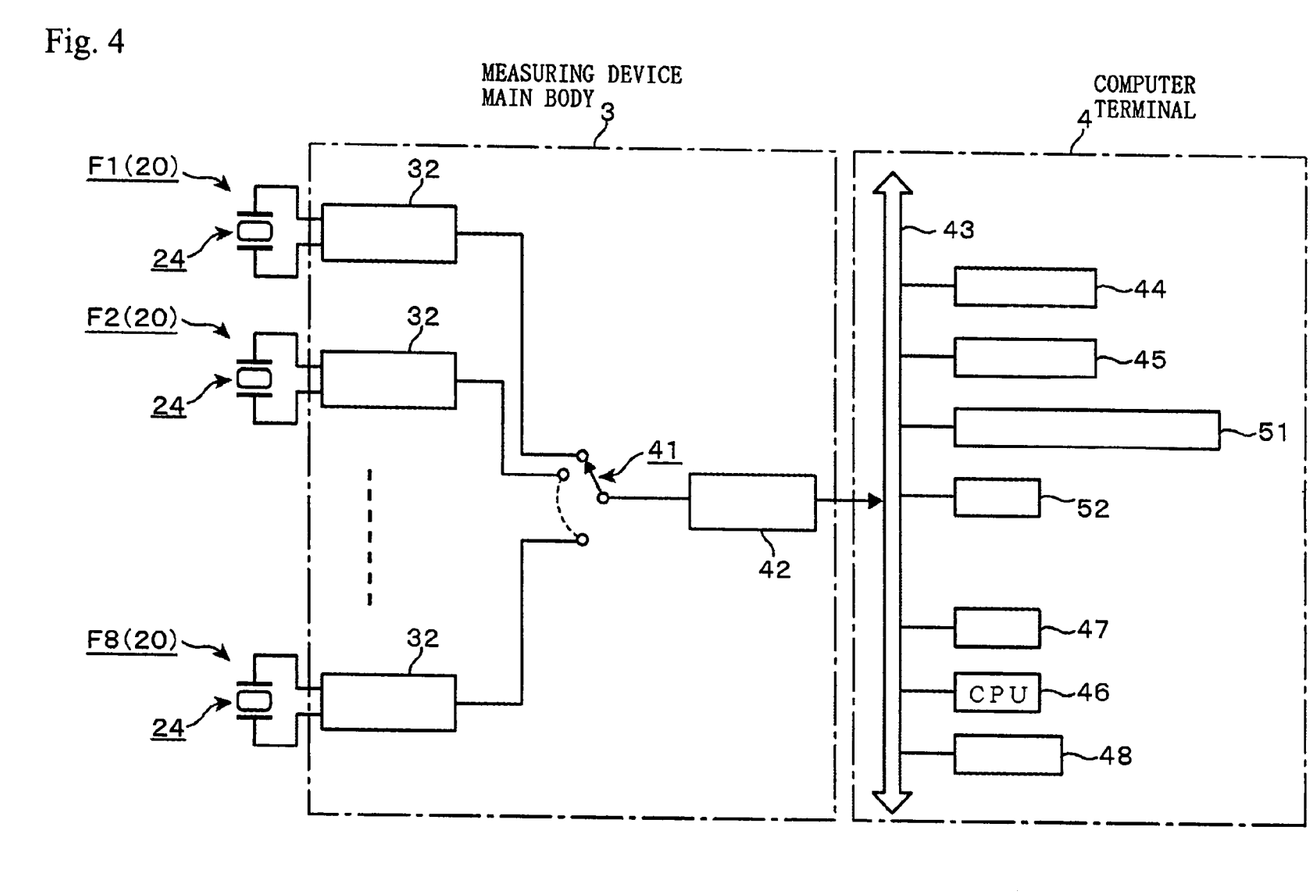
FIG. 4 is a block diagram showing a structure of the sensing device.

FIG. 4 is a block diagram of the sensing device 2. In this block diagram, the eight quartz sensors 20 mounted to the measuring device main body 3 are denoted by F1 to F8 for convenience sake. The quartz sensors F1 to F8 are used as the sensing sensors each detecting the variation of frequencies by making the antigen being the substance to be absorbed in the sample solution absorbed into the absorption layer formed on the surface of the electrode 24a.

Next, the measuring device main body 3 will be described. As shown in FIG. 4, the measuring device main body 3 includes oscillation circuits 32 for oscillating the quartz sensors F1 to F8 respectively, and when the quartz sensors F1 to F8 are inserted into insertion ports thereof shown in FIG. 1, not-shown terminal parts provided in the insertion ports and the printed wirings 27a and 27b of the quartz sensors F1 to F8 are electrically connected. Accordingly, the quartz sensors F1 to F8 are electrically connected to the oscillation circuits 32 respectively, resulting in the oscillation of the respective quartz resonators 20. Then, frequency signals of the respective quartz sensors F1 to F8 are output to a measuring circuit section 42. In this example, the measuring circuit section 42 analog/digital-converts (A/D-converts) a frequency signal being an input signal from the oscillation circuit 32, and performs certain signal processing on the resultant digital signal, thereby detecting the frequency. As a method of performing processing on the frequency signals of the respective quartz sensors F1 to F8 to measure frequencies in main modes of the quartz resonators, the one disclosed in, for example, Japanese Patent Application Laid-open No. 2006-258787 can be adopted, and, for instance, it is also possible that a frequency signal from the oscillation circuit is divided to generate a pulse signal corresponding to the divided frequency signal, and a pulse of the pulse signal is counted by a pulse counter. Further, on a preceding stage of the measuring circuit section 42, a switch section 41 is provided to sequentially acquire output signals from the oscillation circuits 32 corresponding to the respective quartz sensors F1 to F8.

Next, the computer terminal 4 will be described. The computer terminal 4 includes a data bus 43 as shown in FIG. 4, and a first storage section 44, a second storage section 45, a frequency information generating program 51, an editor 52, the aforementioned measuring circuit section 42, a CPU (central processing unit) 46, a display section 47 such as a monitor, and an input unit 48 such as a keyboard are connected to the data bus 43.

The frequency information generating program 51 is configured such that it can obtain pieces of time-series data of oscillation frequencies of the quartz sensors F1 to F8 based on signals output from the measuring circuit section 42, and display the data on the display section 47. The editor 52 has a function such as combining the pieces of time-series data based on absorption start points set in the data to obtain combined data, and displaying the combined data on the display section 47. The first storage section 44 stores the pieces of time-series data of the frequencies of the quartz sensors F1 to F8 obtained by the frequency information generating program 51. The second storage section 45 stores the combined data obtained by the editor 52.

Figure 5:
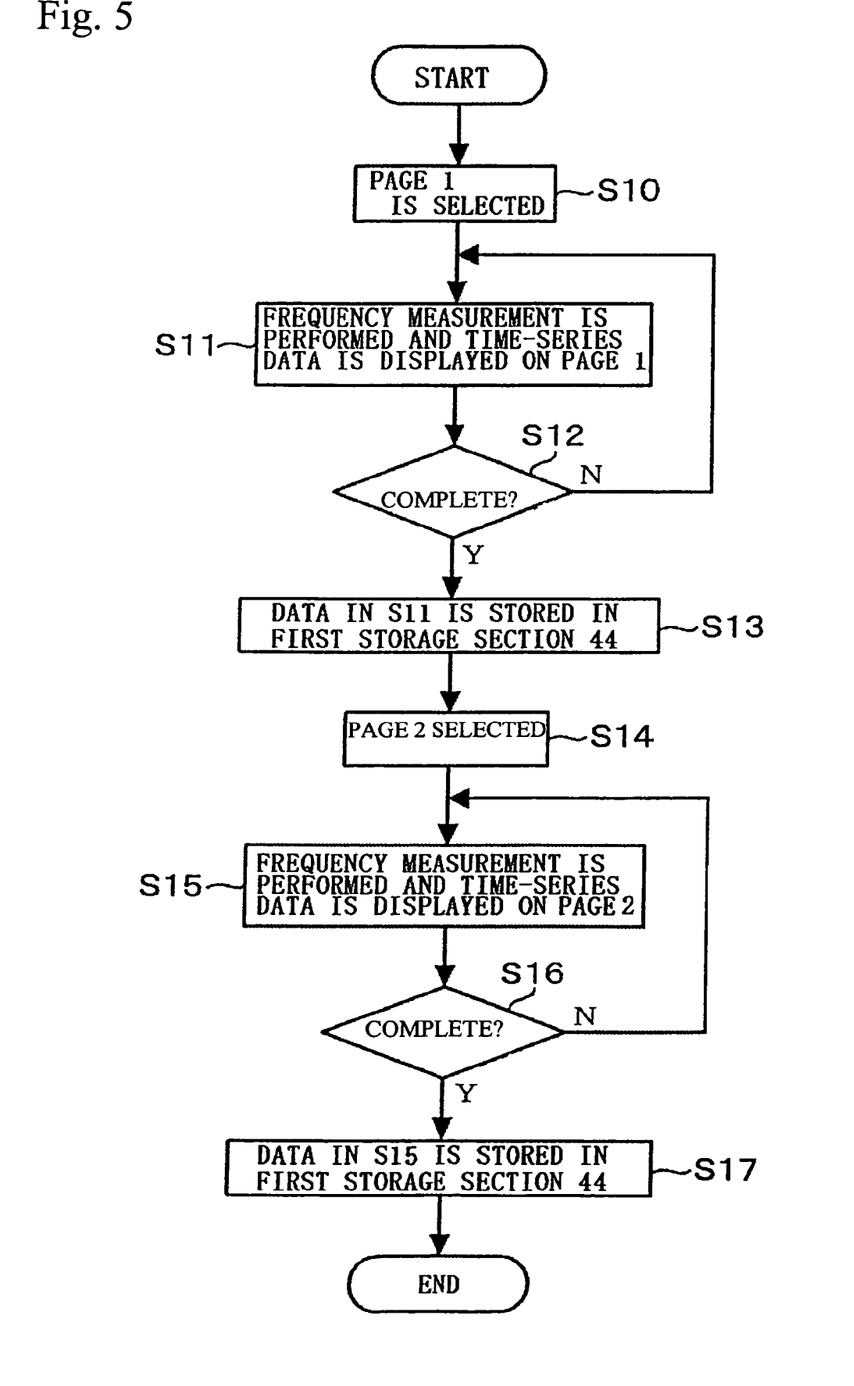
FIG. 5 is a flow chart showing a procedure for performing measurement using the sensing device.
Figure 6:
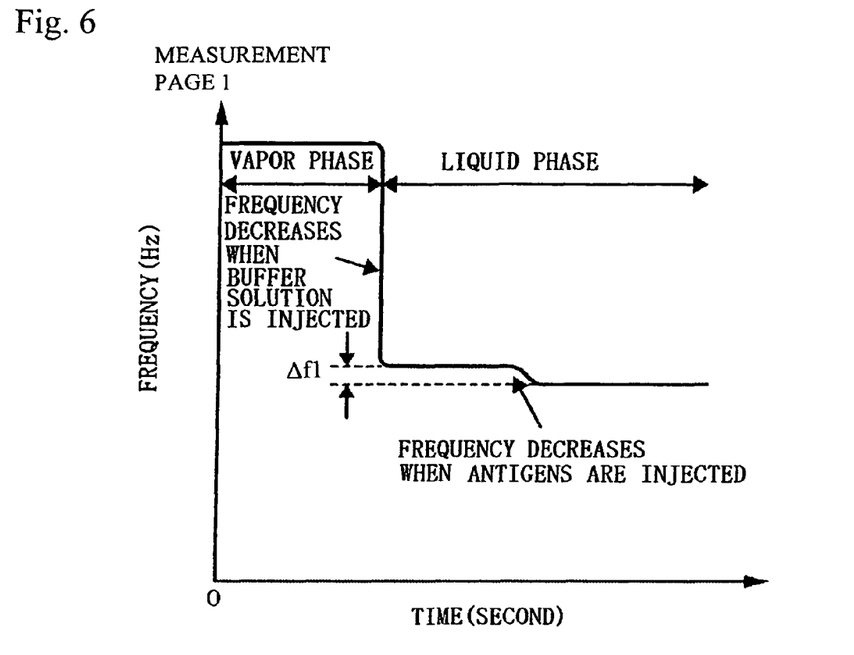
FIG. 6 is a graphic diagram of time-series data obtained by the sensing device.
Figure 8:
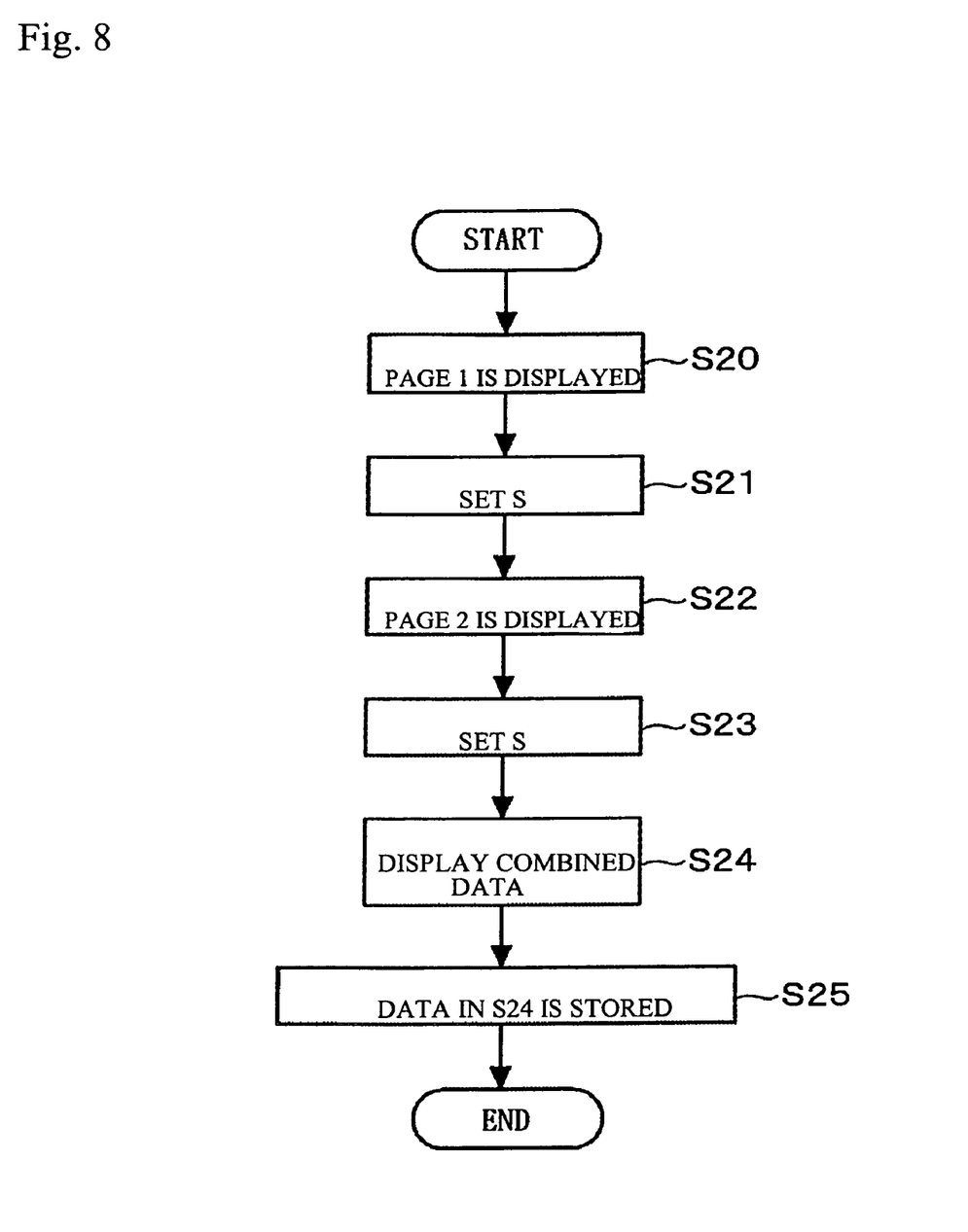
FIG. 8 is a flow chart showing a procedure for performing measurement using the sensing device.

Next, an operation of the sensing device 2 structured as above will be explained with reference to the flow charts shown in FIG. 5 and FIG. 8. First, as shown in FIG. 1, the quartz sensors F1 to F8 are inserted into the insertion ports of the measuring device main body 3. Consequently, the oscillation circuits 32 of respective channels oscillate. Further, in accordance with the oscillation of the oscillation circuits 32 of the respective channels, eight tags of measurement pages respectively corresponding to each of the quartz sensors F1 to F8 are displayed on the display section 47 of the computer terminal 4. Next, the tag of the measurement page 1, for instance, is selected by the input unit 48 of the computer terminal 4, and the frequency measurement using the quartz sensor F1 is conducted (step 10). The frequency measurement will be described using FIG. 6. First, a predetermined amount, for instance, 0.05 ml of buffer solution is injected into the injection port 25a of the quartz sensor F1. Consequently, an environmental atmosphere of the quartz resonator 24 changes from a vapor phase to a liquid phase, and the oscillation frequency of the quartz resonator 24 decreases according thereto. Subsequently, a predetermined amount, for instance, 0.05 ml of sample solution containing 0.01 μg/ml of antigens such as, for instance, dioxins is injected into the injection port 25a of the quartz sensor F1. The dioxin is captured by the absorption layer on the surface of the quartz resonator 24 through a selective capture of molecules by anti-dioxin antibodies, and the oscillation frequency of the quartz resonator 24 is varied by $\Delta f1$ according to the absorption amount of dioxin, as shown in FIG. 6. At a loop formed by steps 11 and 12, time-series data of the frequencies of the quartz sensor F1 shown in FIG. 6 is displayed on the measurement page 1. Subsequently, after the frequency measurement in the quartz sensor F1 is completed (step 12), the time-series data of the frequencies of the quartz sensor F1 is stored in the first storage section 44 (step 13).

Figure 7:
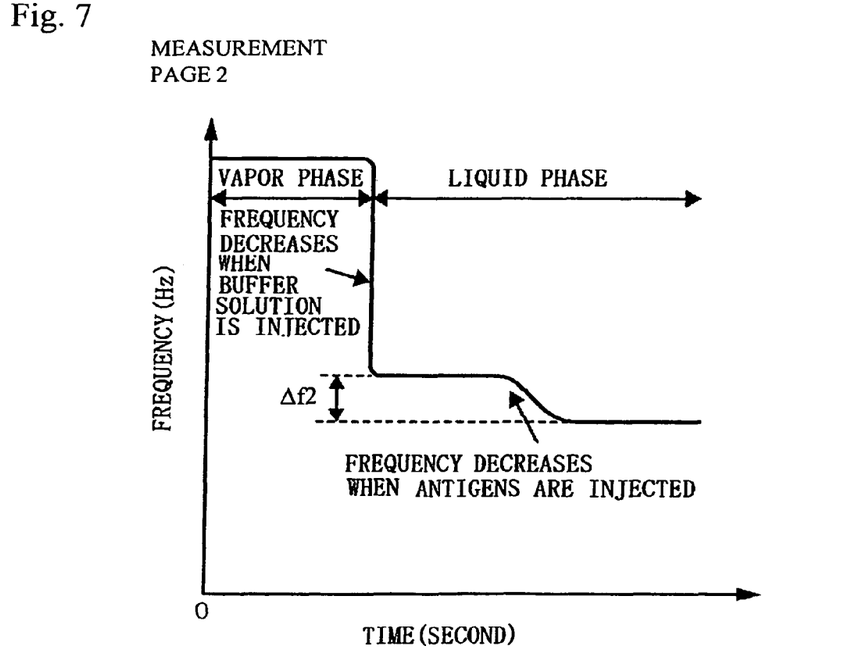
FIG. 7 is a graphic diagram of time-series data obtained by the sensing device.

Next, the tag of the measurement page 2, for instance, is selected by the input unit 48 of the computer terminal 4, and the frequency measurement using the quartz sensor F2 is conducted (step 14). The frequency measurement is performed by following the same procedure as that described above, except that the concentration of dioxin is set as 0.05 μg/ml. In the frequency measurement, the oscillation frequency of the quartz resonator 24 is varied by $\Delta f2$, as shown in FIG. 7. At a loop formed by steps 11 and 12, time-series data of the oscillation frequencies of the quartz sensor F2 shown in FIG. 7 is displayed on the measurement page 2.

Subsequently, after the frequency measurement in the quartz sensor F2 is completed, the time-series data of the frequencies of the quartz sensor F2 is stored in the first storage section 44 (step 17). Note that, also regarding the quartz sensors F3 to F8, the frequency measurement is conducted by varying the concentration of dioxin for each quartz sensor, and pieces of time-series data of frequencies of the respective quartz sensors F3 to F8 are obtained in the same manner, but, in this embodiment, it is assumed that only the time-series data of the frequencies of the quartz sensor F1 and that of the quartz sensor F2 are obtained, and the process proceeds to the next step in which the absorption start point is set in the time-series data, for convenience sake.

Figure 9:
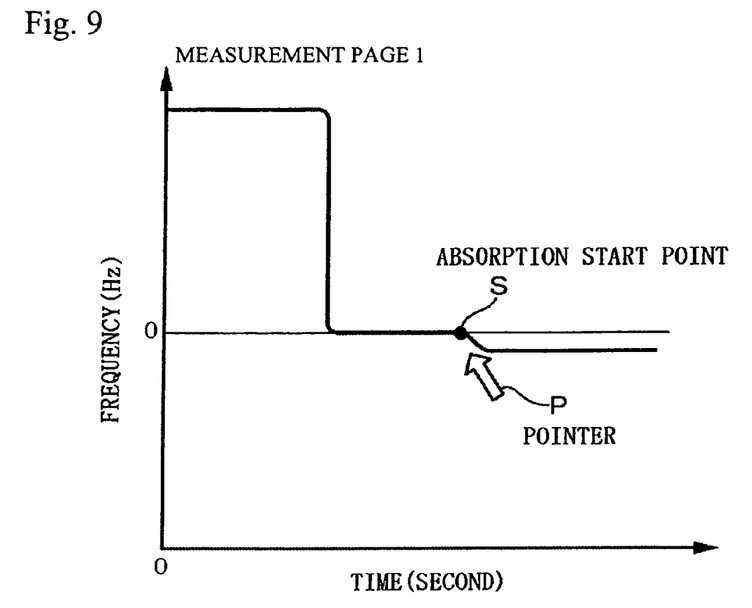
FIG. 9 is a graphic diagram of the time-series data in which an absorption start point is set.

Next, the absorption start point is set in the time-series data stored in the first storage section 44. First, the measurement page 1 is displayed on the display section 47, and the time-series data of the quartz sensor F1 stored in the first storage section 44 (hereinafter, referred to as time-series data 1) is displayed on the measurement page 1 (step 20). Next, as shown in FIG. 9, an operator positions a pointer P displayed on the display section 47 at a point at which the oscillation frequency of the quartz sensor F1 starts to decrease because of the capture of the antigens in the sample solution by the absorption layer on the surface of the quartz resonator 24, and clicks using the input unit 48 of the computer terminal 4. Consequently, an absorption start point S is given at the clicked point (step 21). Further, when the absorption start point S is set in the time-series data 1, the point at which the absorption start point S is given becomes a reference point of frequency and time, and, for instance, the frequency at the reference point in the time-series data 1 is regarded as 0 (zero) Hz for convenience sake, and the time at the reference point is set to be zero. As above, by regarding the frequency at the point at which the absorption start point S is given as "0 (zero) Hz", it becomes easy to observe the frequency variations of the quartz resonators 24 obtained for each concentration of the antigens in later-described combined data. The time-series data 1 in which the absorption start point S is set is stored in the first storage section 44.

Figure 10:
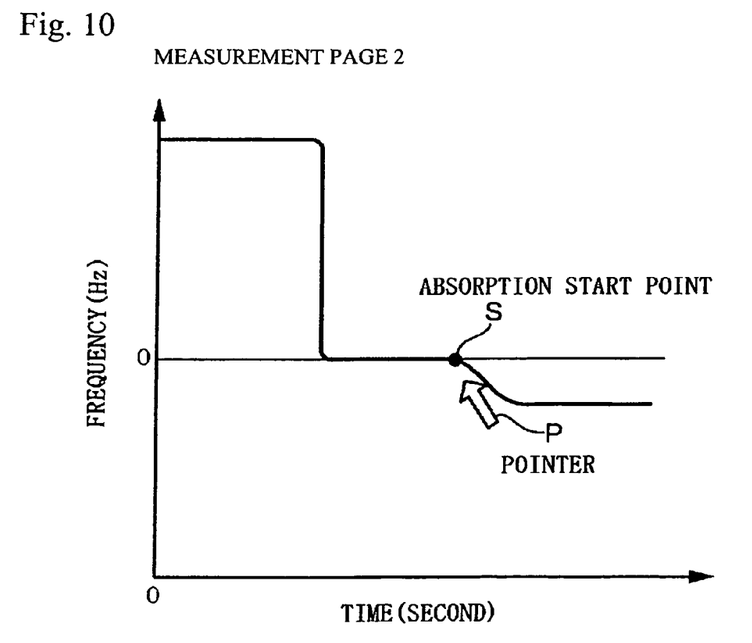
FIG. 10 is a graphic diagram of the time-series data in which an absorption start point is set.

Next, the measurement page 2 is displayed on the display section 47, and the time-series data of the quartz sensor F2 stored in the first storage section 44 (hereinafter, referred to as time-series data 2) is displayed on the measurement page 2 (step 22). Subsequently, as shown in FIG. 10, an absorption start point S is set at a point at which the oscillation frequency of the quartz sensor F2 starts to decrease because of the capture of the antigens in the sample solution by the absorption layer on the surface of the quartz resonator 24 in the same manner as described above, and a frequency at the point at which the absorption start point S is given is set as "0 (zero) Hz" (step 23). The time-series data 2 in which the absorption start point S is set is stored in the first storage section 44.

Figure 11:
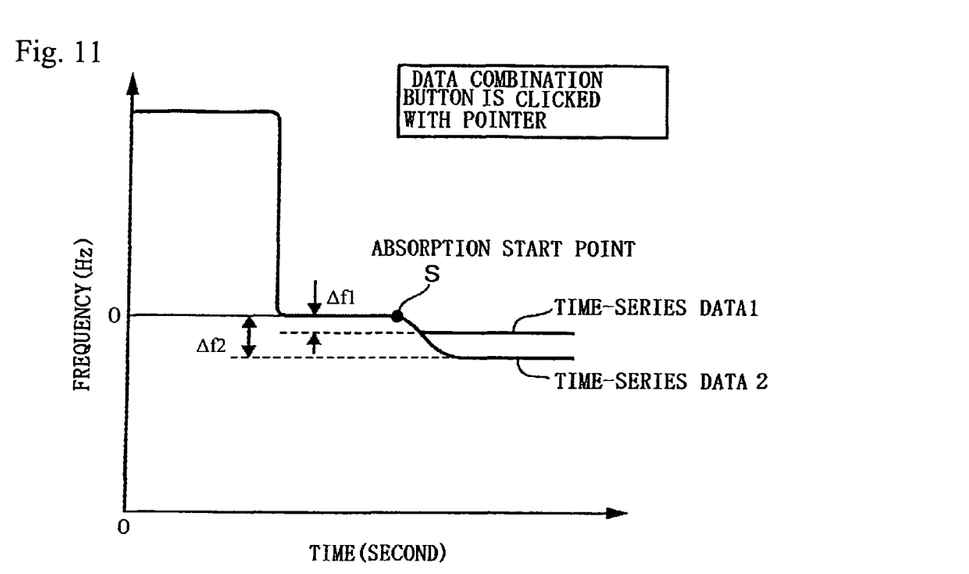
FIG. 11 is a graphic diagram of combined data in which the pieces of time-series data are combined based on the absorption start points set therein.

Subsequently, by clicking a button of "data combination" displayed on the display section 47 with the pointer P, the combination of the time-series data 1 and the time-series data 2 is performed by the aforementioned editor 52 based on the absorption start points S set in the time-series data 1 and 2, and thereafter, the combined data in which the time-series data 1 and the time-series data 2 are combined based on the absorption start points S is displayed on the display section 47, as shown in FIG. 11 (step 24). Then, the combined data is stored in the second storage section 45 (step 25).

Figure 12:
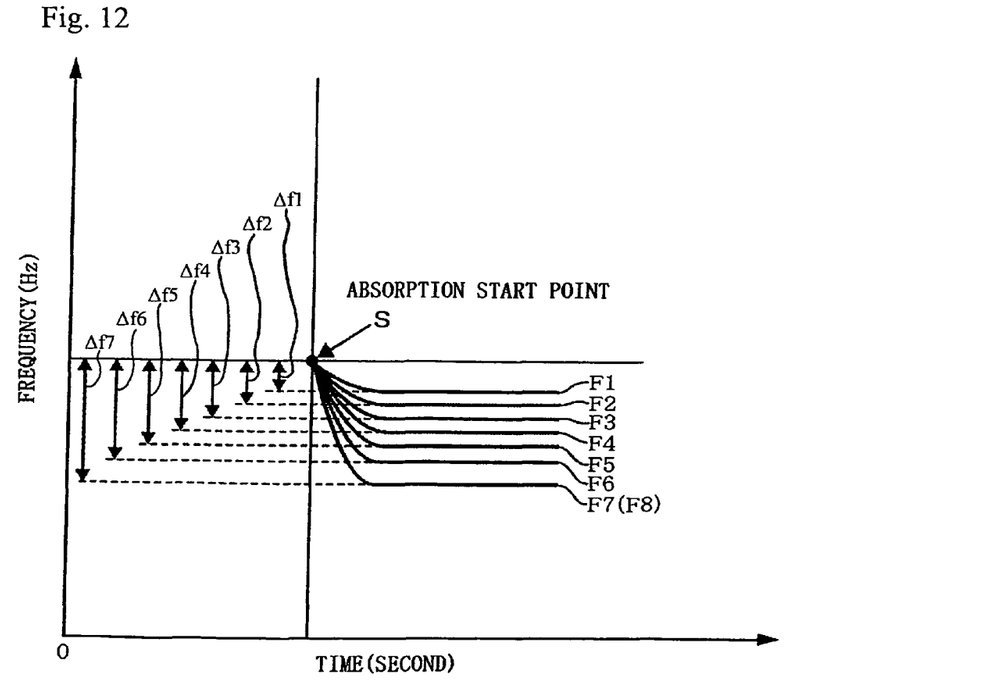
FIG. 12 is a graphic diagram of combined data in which pieces of time-series data are combined based on absorption start points set therein.

FIG. 12 shows combined data in which the frequency measurement is actually performed on the quartz sensors F1 to F8, an absorption start point S is set in pieces of time-series data of frequencies of the respective quartz sensors F1 to F8, and the pieces of time-series data are combined based on the absorption start points S. In the combined data shown in FIG. 12, only frequency variation regions in the pieces of time-series data are combined in a state of aligning the absorption start points S. Here, describing the combined data shown in FIG. 12, it can be confirmed that the frequency variation amount Δf from the absorption start point S is gradually increased as the concentration of the antigens injected into the buffer solution in the quartz sensor 20 is gradually increased. Further, since the quartz sensor F7 and the quartz sensor F8 have the same frequency variation amount Δf7 from the absorption start point S, it can be confirmed that the concentration of dioxin contained in the sample solution used for the quartz sensor F7 corresponds to the maximum absorption amount of dioxin capable of being absorbed into the absorption layer on the surface of the quartz resonator 24.

According to the aforementioned embodiment, it is designed such that the absorption start point S is set in the pieces of time-series data of the frequencies of the quartz resonators 24 obtained for each concentration of the antigens, which are dioxins in this example, and the combined data in which the pieces of time-series data are combined based on the absorption start points S is displayed on the display section 47. Accordingly, it is possible to easily determine the correspondence between the concentration of dioxin absorbed into the absorption layer on the surface of the quartz resonator 24 and the variation of frequencies, and the maximum absorption amount of dioxin, which is very convenient.

Figure 18:
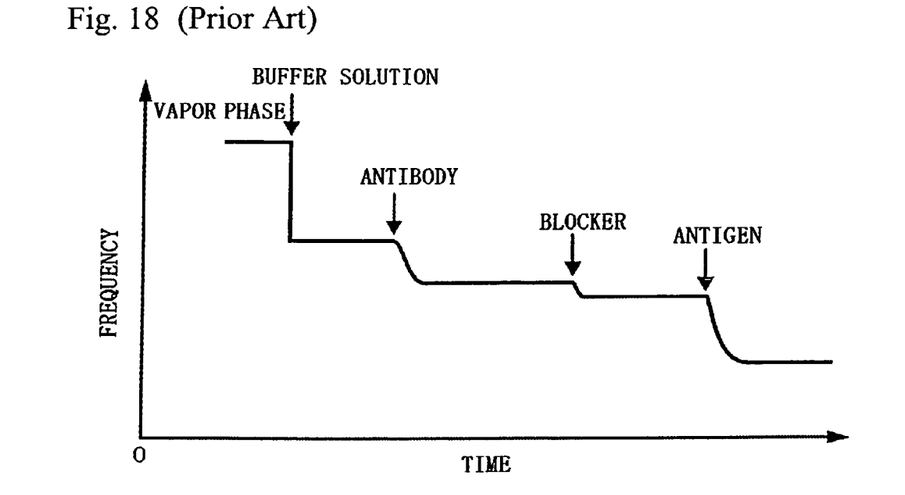
FIG. 18 is a graphic diagram showing a frequency variation of the quartz resonator at the time of manufacturing the quartz sensor and a frequency variation at the time of measurement using the manufactured quartz sensor.

Further, as an application example of the present invention, it is possible, also in the manufacturing stage of the quartz sensor 20, to similarly set an absorption start point S in pieces of time-series data of frequencies of the quartz resonators 24 obtained for each concentration of antibodies or blockers and display combined data in which the pieces of time-series data are combined based on the absorption start points S on the display section 47, as explained in the description of the related art using FIG. 18. In this case, it is possible to determine the correspondence between the concentration of the antibodies or blockers absorbed into one electrode surface of the quartz resonator 24 and the variation of frequencies, and the maximum absorption amount of the antibodies or blockers.

Figure 13:
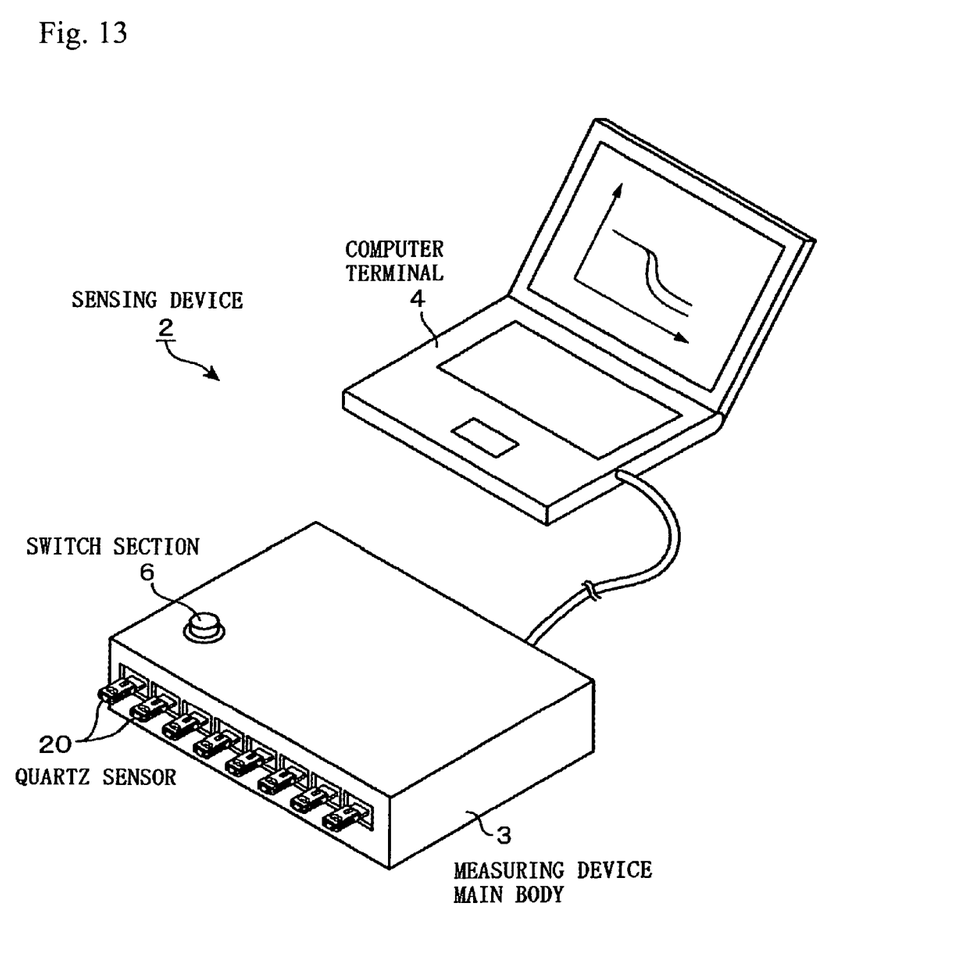
FIG. 13 is a whole structural diagram of a sensing device according to another embodiment of the present invention.
Figure 14:
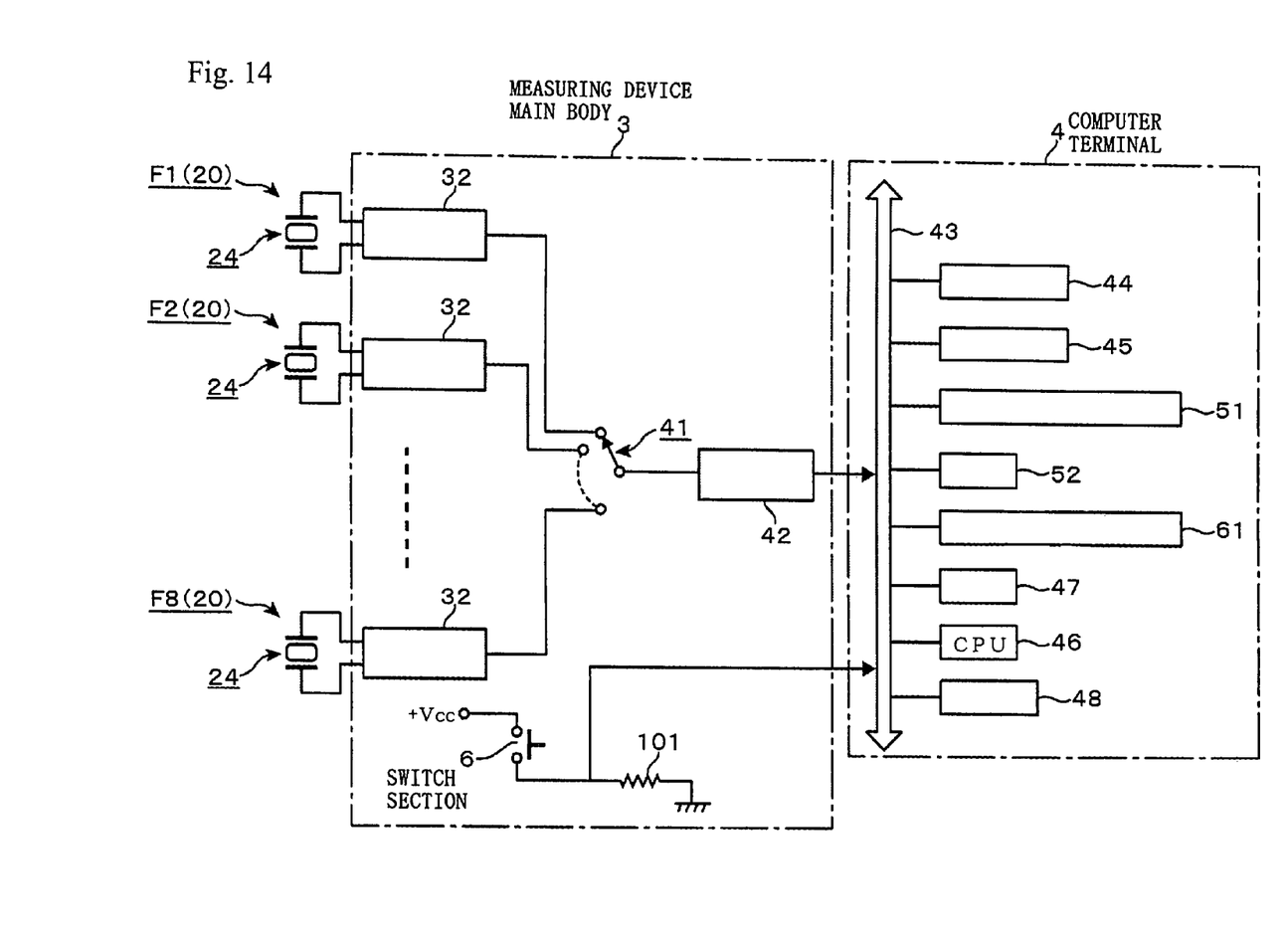
FIG. 14 is a block diagram showing a structure of the sensing device.
Figure 15:
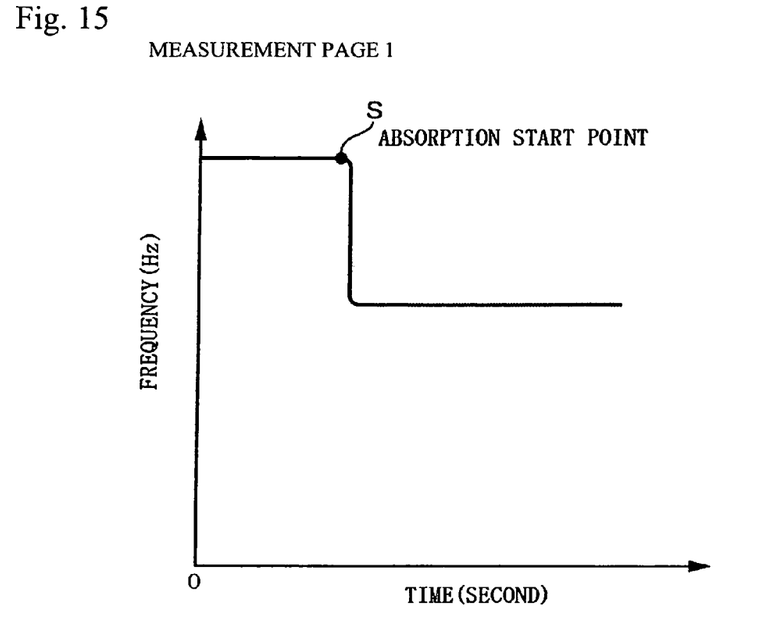
FIG. 15 is a graphic diagram of time-series data obtained by the sensing device.

Another embodiment of the present invention will be described. In this embodiment, a push-button switch section 6 is provided in the measuring device main body 3 as shown in FIG. 13, and it is structured such that when the switch section 6 is turned on, an "ON" signal is input into the computer terminal 4. As shown in FIG. 14, a sensing device of the embodiment has exactly the same structure as that of the sensing device 2 explained using FIG. 1 to FIG. 12, except that an absorption start point setting program 61 is connected to the data bus 43 of the computer terminal 4. Note that 101 in FIG. 14 is a resistance. In this example, when a sample solution containing antigens is injected into, for instance, the injection port 25a of the quartz sensor F1 using, for example, an electric pipette, and at the same time, an operator pushes a button of the switch section 6, the absorption start point S of the antigens is set in the time-series data regarding the frequencies of the quartz resonator 24 of the quartz sensor F1, as shown in FIG. 15. The setting of the absorption start point S is conducted when the operator pushes a switch of the switch section 6, which results in the output of an absorption start signal from the absorption start point setting program 61. Therefore, the editor 52 combines the respective pieces of time-series data based on the absorption start point S set as above. With this structure, it is possible to grasp the absorption start point S of the antigens in the obtained time-series data. Therefore, there is an advantage in that the labor for an operator to position and click, for each page, the pointer P at a point at which the oscillation frequency starts to decrease, can be saved.

Figure 16:
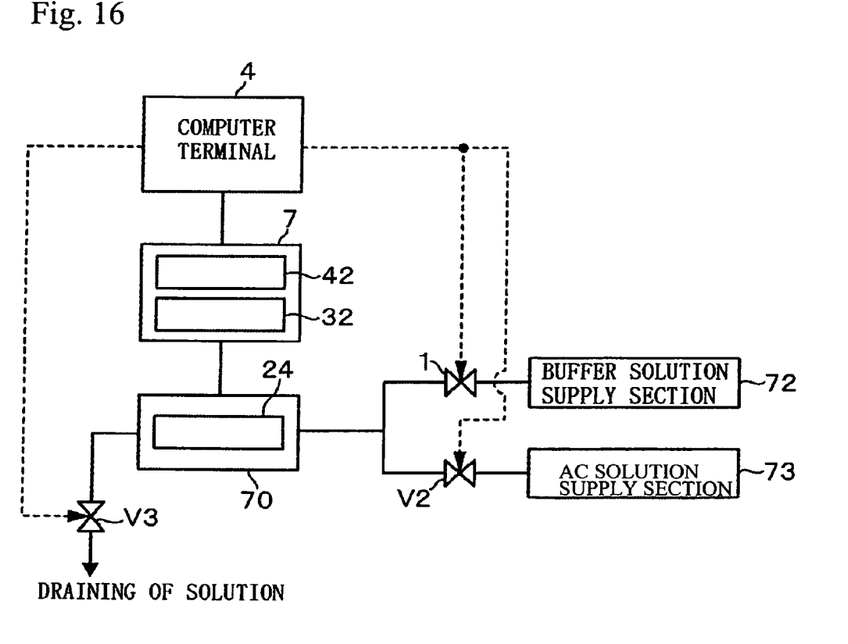
FIG. 16 is a block diagram showing a whole structure of a sensing device according to still another embodiment of the present invention.

Further, the aforementioned measuring device main body 3 is structured such that it includes the eight quartz sensors F1 to F8 as shown in FIG. 1 and FIG. 13 and the frequency measurement is performed on the eight quartz sensors F1 to F8, but, it may be structured such that a cell 70 provided with the quartz resonator 24 is electrically connected to a measuring device main body 7 that includes the oscillation circuit 32 and the measuring circuit section 42, and a buffer solution supply section 72 and an antigen-containing solution supply section 73 are connected to the cell 70, as shown in FIG. 16. The buffer solution supply section 72 includes a container in which the buffer solution is stored, a pump provided in a pipe connected to the container, and the like. Further, the antigen-containing solution supply section 73 includes a container in which the antigen-containing solution is stored, a pump provided in a pipe connected to the container, and the like. As a pump, one called such as a sack-back valve that includes, for instance, a cylinder divided and connected to the pipe, and an operating section that sucks/pushes out the solution into/from the cylinder can be used, but, it is also possible to use a common solution supply pump.

In FIG. 16, V1, V2 and V3 are valves. The respective pumps, the valves V1, V2 and V3 of the buffer solution supply section 72 and the antigen-containing solution supply section 73 are controlled by control signals from the computer terminal 4 being a control section. In such a structure, the frequency measurement is performed as follows. First, the valve V2 is closed, the valves V1 and V3 are opened, and the pump of the buffer solution supply section 72 is driven to inject a predetermined amount of buffer solution into the cell 70. Next, the valve V1 is closed, and the valve V2 is opened to inject a predetermined amount of antigen-containing solution in which the concentration of antigens is adjusted into the cell 70 from the antigen-containing solution supply section 73. Subsequently, after the frequency measurement in the quartz resonator 24 is completed, draining of solution from the cell 70 is performed, and the next frequency measurement is performed in the same procedure by varying the concentration of the antigens. The draining of solution from the cell 70 is conducted, for instance, by making the inside of the cell 70 open to the atmosphere by opening a not-shown valve provided in the cell 70, and also by opening the valve V3.

In this structure, the absorption start point S is automatically output from the computer terminal 4 at a time point little later than a time point at which driving signals of the respective pumps of the buffer solution supply section 72 and the antigen-containing solution supply section 73 are output from the computer terminal 4. The little-later time point is determined by considering a period of time from when the pumps are driven until when the solution is distributed into the cell 70. The output of the absorption start point S is performed based on the recognition of the output of pump driving signals by the absorption start point setting program 61 shown in FIG. 14. With the use of such a method, the measuring operation can be simplified.

Note that if the setting of the absorption start point is automatically performed when the solution is supplied to the sensing sensor, or if the setting is performed when the switch is operated by the operator, it is not necessarily to display the individual pieces of time-series data of the frequencies of the piezoelectric resonators obtained for each concentration of the substance to be absorbed.

The invention claimed is:

1. A sensing device comprising:
a sensing sensor provided with a sensing piezoelectric resonator whose natural frequency is varied by an absorption of a substance to be absorbed;
an oscillation circuit for oscillating the piezoelectric resonator;
a display section for displaying, on mutually differing pages, pieces of time-series data of frequencies of the piezoelectric resonator obtained for each concentration of the substance to be absorbed in solutions, by way of displaying, on mutually differing pages, time-series data for the frequency of the piezoelectric resonator obtained by supplying a fluid containing the substance to be absorbed to first sensing sensor, and time-series data for the frequency of the piezoelectric resonator obtained by supplying a fluid containing the substance to be absorbed at a concentration that differs from the concentration of the substance to be absorbed that was supplied to said first sensing sensor to a second sensing sensor;
a unit for setting absorption start points of the substances to be absorbed in the pieces of time-series data; and
an editor for performing processing to combine and display at least frequency variation regions in the pieces of time-series data in a state of aligning the absorption start points of the substance to be absorbed,
wherein the setting conducted by said unit for setting the absorption start point of the substance to be absorbed is realized when an operator positions a pointer and clicks on the time-series data displayed on said display section.

2. The sensing device according to claim 1,
wherein the setting conducted by said unit for setting the absorption start point of the substance to be absorbed is automatically realized when the solution is supplied to said sensing sensor.

3. The sensing device according to claim 2,
wherein said unit for setting the absorption start point of the substance to be absorbed is a switch operated by an operator.

4. A sensing device comprising:
a sensing sensor provided with a sensing piezoelectric resonator whose natural frequency is varied by an absorption of a substance to be absorbed;
a cell in which said sensing sensor is disposed;
a flow path, provided in order to supply liquid to the interior of the cell, the base end of which branches into a first flow path and a second flow path;
a reference solution supply unit, which supplies a reference solution to the first flow path;
a sample solution supply unit, which supplies sample solution including the substance to be absorbed to the second flow path;
a flow path switching unit, for switching between the first flow path and the second flow path;
an oscillator circuit for oscillating the piezoelectric resonator;
a data capture unit that captures time-series data for the frequency of the piezoelectric vibrator obtained by supplying the sample solution containing the substance to be absorbed to first sensing sensor, and time-series data for the frequency of the piezoelectric resonator obtained by supplying the sample solution containing the substance to be absorbed at a concentration that differs from the concentration of the substance to be absorbed that was supplied to said first sensing sensor to a second sensing sensor;
a control unit for performing control so that the reference solution is supplied to the interior of the cell via the first flow path, and then the sample solution is supplied to the interior of the cell via the second flow path; and
an editor for performing processing to use the point in time at which a predetermined amount of time has passed since starting at the supply of sample solution from the sample solution supply part as the absorption start point, and combine and display at least frequency variation regions in the pieces of time-series data in a state of aligning the absorption start points of the substance to be absorbed.

* * * * *